(12) United States Patent
Reinstein et al.

(10) Patent No.: US 10,813,708 B2
(45) Date of Patent: Oct. 27, 2020

(54) REMOTE ROBOTIC ACTUATION OF A TRANSESOPHAGEAL ECHOCARDIOGRAPHY PROBE

(71) Applicant: KONINKLIJKE PHILIPS N.V., Eindhoven (NL)

(72) Inventors: Aryeh Leib Reinstein, Bronx, NY (US); Aleksandra Popovic, Boston, MA (US); David Paul Noonan, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 239 days.

(21) Appl. No.: 15/535,281

(22) PCT Filed: Dec. 8, 2015

(86) PCT No.: PCT/IB2015/059426
§ 371 (c)(1),
(2) Date: Jun. 12, 2017

(87) PCT Pub. No.: WO2016/097926
PCT Pub. Date: Jun. 23, 2016

(65) Prior Publication Data
US 2017/0360518 A1 Dec. 21, 2017

Related U.S. Application Data

(60) Provisional application No. 62/092,299, filed on Dec. 16, 2014.

(51) Int. Cl.
*A61B 34/37* (2016.01)
*A61B 8/12* (2006.01)
(Continued)

(52) U.S. Cl.
CPC ............... *A61B 34/37* (2016.02); *A61B 8/12* (2013.01); *A61B 8/467* (2013.01); *A61B 34/74* (2016.02);
(Continued)

(58) Field of Classification Search
CPC ......... A61B 34/37; A61B 8/467; A61B 34/74; A61B 8/12; A61B 2090/3784;
(Continued)

(56) References Cited

U.S. PATENT DOCUMENTS 6,425,865 B1 7/2002 Salcudean
6,726,675 B1 4/2004 Beyar
(Continued)

FOREIGN PATENT DOCUMENTS

EP 1782744 A2 5/2007
JP H0288025 A 3/1990
(Continued)

*Primary Examiner* — Jason Holloway (57) ABSTRACT

A replica control tool (70) for remotely controlling a control handle (42) of an interventional tool (e.g., a probe, a catheter and a flexible scope) is robotically controlled by a robotic actuator (50). The replica control tool (70) employs a replica control handle (71) is substantially a replica of a structural configuration of the control handle (42) of the interventional tool. A control input device (72) (e.g., a joystick or a trackball) is movable relative to the replica control handle (71). The replica control tool (70) further employs a robotic actuator controller (75) for remotely controlling the robotic actuator (50) in response to any movement of the control input device (72) relative to the replica control handle. The replica control tool (70) may further employ an electromechanical device (73) (e.g., an accelerometer) co-rotatable with the replica control handle (71) whereby the controller (75) remotely controls the robotic actuator (50) in response to a rotation of the electromechanical device (73).

16 Claims, 4 Drawing Sheets

(51) Int. Cl.
  *A61B 34/00* (2016.01)
  *A61B 8/00* (2006.01)
  *B25J 13/02* (2006.01)
  *A61B 18/00* (2006.01)
  *A61B 34/30* (2016.01)
  *A61B 90/00* (2016.01)

(52) U.S. Cl.
  CPC ..... *B25J 13/02* (2013.01); *A61B 2018/00303* (2013.01); *A61B 2034/301* (2016.02); *A61B 2090/3784* (2016.02)

(58) Field of Classification Search
  CPC .... A61B 2034/301; A61B 2018/00303; A61B 2017/00469; A61B 5/6852; B25J 13/02; A61M 25/0136; A61M 25/0105; A61M 25/0133
  See application file for complete search history.

(56) References Cited

U.S. PATENT DOCUMENTS

| | | | |
|---|---|---|---|
| 7,641,650 B2 | 1/2010 | Boese | |
| 7,753,851 B2 | 7/2010 | Nilsson | |
| 8,257,302 B2 | 9/2012 | Beyar | |
| 8,740,840 B2 | 6/2014 | Foley | |
| 8,961,533 B2* | 2/2015 | Stahler | A61B 6/12 606/108 |
| 9,265,581 B2* | 2/2016 | Navve | A61B 34/70 |
| 10,010,699 B2 | 4/2018 | Cohen | |
| 2002/0177843 A1* | 11/2002 | Anderson | A61B 17/320068 606/1 |
| 2007/0043338 A1* | 2/2007 | Moll | A61B 17/062 606/1 |
| 2007/0233044 A1* | 10/2007 | Wallace | A61B 5/6885 604/528 |
| 2008/0009791 A1* | 1/2008 | Cohen | A61M 25/0105 604/95.01 |
| 2012/0071752 A1* | 3/2012 | Sewell | A61B 6/12 600/424 |
| 2012/0078080 A1* | 3/2012 | Foley | A61B 34/74 600/411 |
| 2012/0143353 A1 | 6/2012 | Kishi | |
| 2012/0184955 A1* | 7/2012 | Pivotto | A61B 34/74 606/41 |
| 2013/0002895 A1 | 1/2013 | Mcclung | |
| 2013/0172906 A1 | 7/2013 | Olson | |
| 2014/0276392 A1 | 9/2014 | Wong | |
| 2014/0316433 A1* | 10/2014 | Navve | A61B 34/70 606/130 |
| 2015/0230697 A1* | 8/2015 | Phee | A61B 1/00135 600/106 |
| 2017/0157361 A1* | 6/2017 | Barrish | A61B 34/20 |

FOREIGN PATENT DOCUMENTS

| | | |
|---|---|---|
| WO | 2009120948 A2 | 10/2009 |
| WO | 2010078344 A1 | 7/2010 |

\* cited by examiner

REMOTE ROBOTIC ACTUATION OF A TRANSESOPHAGEAL ECHOCARDIOGRAPHY PROBE

CROSS-REFERENCE TO PRIOR APPLICATIONS

This application is the U.S. National Phase application under 35 U.S.C. § 371 of International Application No. PCT/IB2015/059426, filed on Dec. 8, 2015, which claims the benefit of U.S. Provisional Patent Application No. 62/092,299, filed on Dec. 16, 2014. These applications are hereby incorporated by reference herein.

FIELD OF THE INVENTION

The present invention generally relates to transeesophageal echocardiography ("TEE") probes. The present invention specifically relates to a remote robotic actuation of the TEE probe during an interventional procedure.

BACKGROUND OF THE INVENTION

Figure 1:
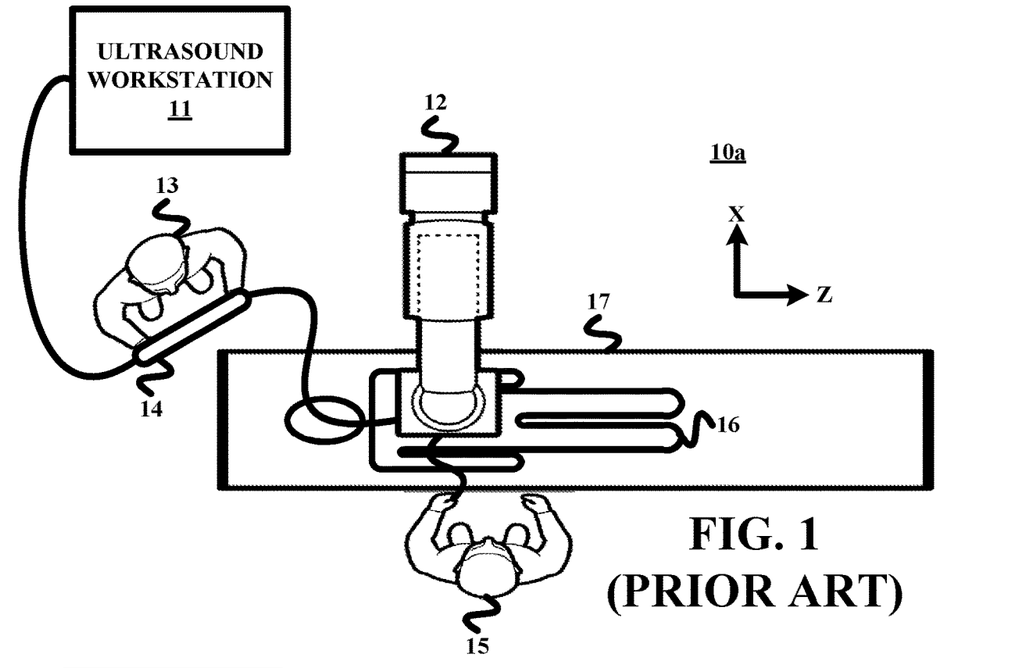
FIG. 1 illustrates an exemplary manual actuation of a TEE probe as known in the art.

Transesophageal echocardiography is commonly used to visualize cardiac anatomy and interventional devices during treatment for structural heart disease ("SHD"). FIG. 1 shows a typical distribution of theatre staff within a lab room 10a having an ultrasound workstation 11 and an x-ray scanner, of which a c-arm 12 is shown. During a SHD operation, an echocardiographer 13 holds a TEE probe 14, which passes through a mouth of a patient 16 into an esophagus to visualize a heart of patient 16. A cardiologist 15 is located on an opposite side of x-ray c-arm 12 and an operating table 17. Cardiologist 15 navigates interventional devices (not shown) (e.g., catheters and guidewires) from arterial incisions into the heart under x-ray guidance and ultrasound guidance via TEE probe 14 in order to perform different diagnostic or therapeutic procedures. Exemplar procedures, such as mitral clip deployments or transcatheter aortic valve replacements ("TAVR"), can be time consuming and complex. Moreover, ensuring appropriate visualization of the target anatomy during the procedure is the responsibility of echocardiographer 13, who must make constant small adjustments to a position of a tip of TEE probe 14 for the duration of the procedure.

In practice, the operating conditions of FIG. 1 present several challenges. The first challenge is fatigue and poor visualization. Specifically, appropriate visualization includes both ensuring the relevant anatomical structures are within the field of view, and that the necessary contact force between the transducer head and esophageal wall, to achieve adequate acoustic coupling, is achieved. To this end, a position and an orientation of a head of TEE probe 14 requires constant, minute adjustments for the duration of the procedure in order to maintain appropriate visualization of the target structures. This can lead to fatigue and poor visualization by echocardiographer 13 during long procedures.

The second challenge is x-ray exposure. Specifically, a length of TEE probe 14 results in the positioning of echocardiographer 13 in close proximity to the source of interventional x-ray system, thus maximizing the x-ray exposure of echocardiographer 13 over the course of the procedure.

The third challenge is communication and visualization. During certain phases of a procedure, cardiologist 15 and echocardiographer 13 must be in constant communication as cardiologist 15 instructs echocardiographer 13 as to which structure to visualize. Given the difficulty interpreting a 3D ultrasound volume, and the different co-ordinate systems displayed by the x-ray and ultrasound systems, it can be challenging for echocardiographer 13 to understand the intentions of cardiologist 15.

SUMMARY OF THE INVENTION

Figure 2:
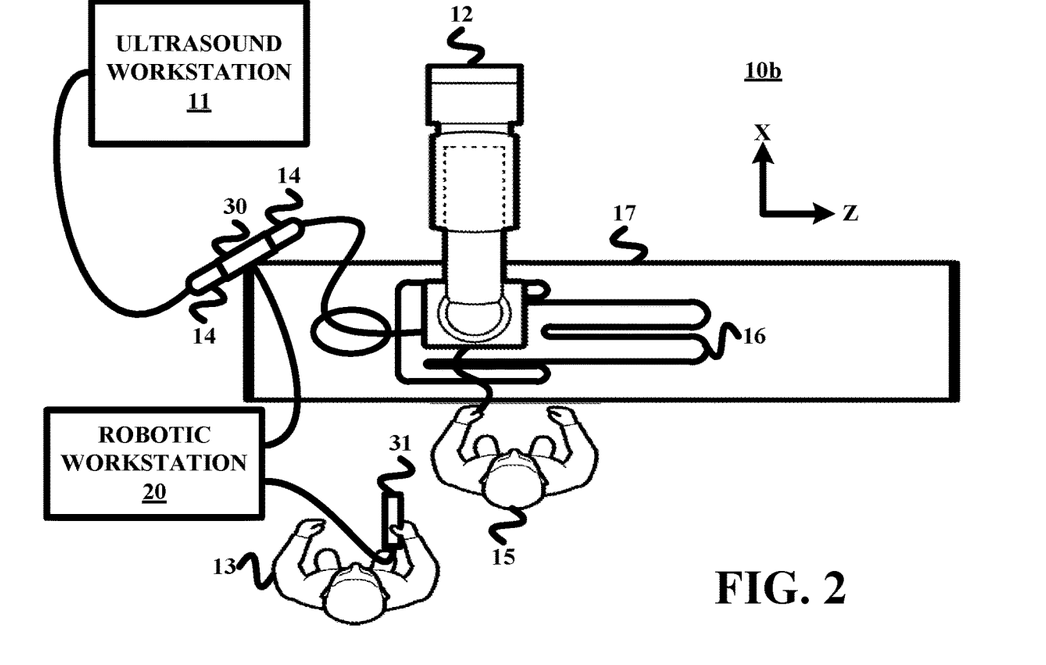
FIG. 2 illustrates an exemplary embodiment of a remote controlled actuation of a TEE probe in accordance with the present invention.

The present invention provides a remote robotic actuation system to address operational challenges associated with an interventional tool, particularly a TEE probe. Generally, as shown in FIG. 2, a new distribution of theatre staff within a lab room 10b with the remote robotic actuator system employing a robotic workstation 20, a robotic actuator 30, and a replica TEE control tool 31 and for remote actuation of between two (2) degrees of freedom and (4) degrees of freedom of TEE probe 14, which adjust the ultrasound imaging volume of TEE probe 14. Additionally, as will be further described herein, replica TEE control tool 31 may have the ability to be employed for use with existing and various types of robotic actuators 30, and may have the ability to be rapidly disengaged from robotic actuator 30 should echocardiographer 13 decide to return to manual operation of TEE probe 14 for any reason.

One form of the present invention is a replica control tool for remotely controlling a robotic actuator that robotically controls a control handle of an interventional tool (e.g., a probe, a catheter, flexible scopes, etc.), which in turn actuates a distal end of the interventional tool. The replica control tool employs a replica control handle substantially being a replica of a structural configuration of the control handle of the interventional tool, and a control input device (e.g., a joystick or a trackball) movable relative to the replica control handle. The replica control tool further employs a robotic actuator controller for remotely controlling a deflection of a distal end of the interventional tool by the robotic actuator responsive to any movement of the control device relative to the replica control handle. The replica control tool further employs an electromechanical device (e.g., an accelerometer) co-rotatable with the replica control handle whereby the robotic actuator controller further remotely controls a rotation of the distal end of the interventional tool by the robotic actuator in response to a co-rotation of the electromechanical device with the replica control handle.

For purposes of the present invention, the term "controller" broadly encompasses all structural configurations of an application specific main board or an application specific integrated circuit housed within or linked to a computer or another instruction execution device/system for controlling an application of various inventive principles of the present invention as subsequently described herein. The structural configuration of the application controller may include, but is not limited to, processor(s), computer-usable/computer readable storage medium(s), an operating system, peripheral device controller(s), slot(s) and port(s). Examples of a computer include, but are not limited to, a server computer, a client computer, a workstation and a tablet.

A second form of the present invention is a robotic actuation system employing the robotic actuator and the replica control tool.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

DETAILED DESCRIPTION OF THE PREFERRED EMBODIMENTS

Figure 3:
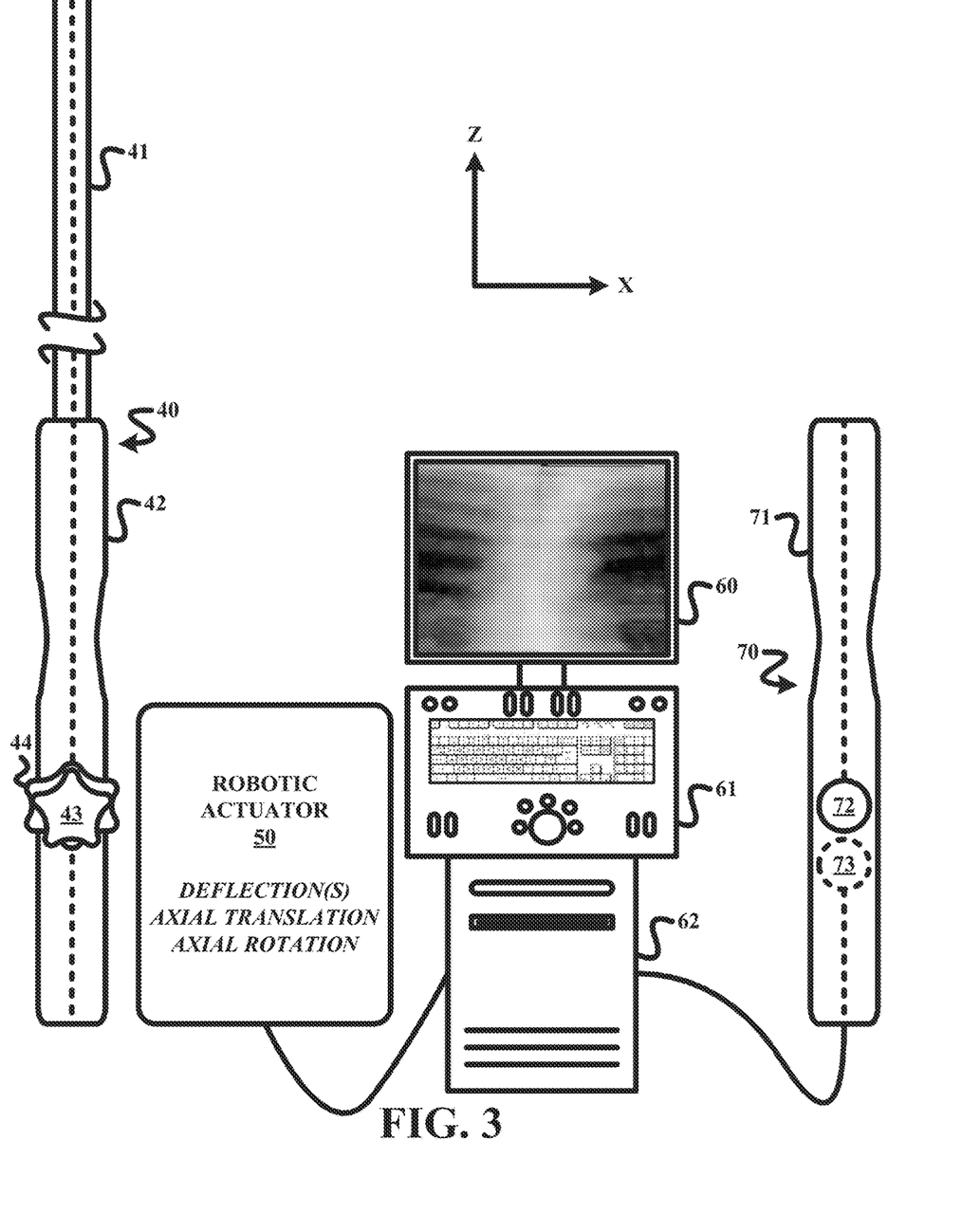
FIG. 3 illustrates an exemplary embodiment of a robotic actuation system in accordance with the present invention.

To facilitate an understanding of the present invention, exemplary embodiments of a robotic actuation system of the present invention and various components therefore will now be described in the context of a remote control actuation of a TEE probe as shown in FIG. 3. From these descriptions, those having ordinary skill in the art will appreciate how to apply the principles of a robotic actuation system of the present invention to any suitable designs of ultrasound probes for any type of procedure as well as other tendon driven flexible interventional tools (e.g., a catheter, an endoscope, a colonoscope, a gastroscope, a bronchoscope, etc.).

For purposes of the present invention, the terms of the art including, but not limited to, "deflection", "joystick", "accelerometer", "light emitting diode", "actuation", "robotic", "robotic actuator", "workstation", "input device" and "electromechanical device" are to be interpreted as known in the art of the present invention.

Referring to FIG. 3, a TEE probe 40 as known in the art employs an elongated probe 41 and a control handle 42 having a yaw actuation dial 43 for adjusting a yaw degree freedom of a distal tip of probe 41 and a pitch actuation dial 44 for adjusting a pitch degree freedom of the distal tip of probe 41.

A robotic actuator 50 as known in the art provides a mechanical control of yaw actuation dial 43 and pitch actuation dial 44 for deflecting the distal tip of probe 41 in an anterior direction, a posterior direction, a lateral left direction, a lateral right direction or a combination thereof.

Robotic actuator 50 as known in the art may further provide a mechanical control of a translation along and/or a rotation about a longitudinal axis of TEE probe 40 as symbolically shown by the dashed line extending through TEE probe 40.

A robotic workstation 62 as known in the art has controller(s) installed therein for communicating control commands to robotic actuator 50 via an operator's use of an interface platform 61. Typically, the operator will interact with interface platform 61 to strategically navigate probe 41 via selective deflections, translations and/or rotations of probe 41 within a patient as illustrated by on overlay of probe 41 on a x-ray image or other volume image displayed by a monitor 60.

The present invention provides a replica TEE control tool 70 having a replica control handle 71 substantially being a replica of a structural configuration of TEE control handle 42. In practice, replica control handle 71 may be constructed in the same manner as TEE control handle 42 with the inside of replica control handle 71 being hollowed out for placement of electronic, electromechanical, mechanical and/or other components for implementing the inventive principles of the present invention.

One such inventive principle of the present invention is the replacement of dials 43 and 44 with a control input device 72 including, but not limited to, duplicates of dials 43 and 44, a two-axis thumb joystick and/or a two-axis tracker ball. Control input device 72 allows for an easy and more intuitive control of probe 41. Specifically, lateral left-right motion of control input device 72 is mapped to a lateral left-right deflection of probe 41, and an up-down motion of control input device 72 is mapped to an anterior-posterior deflection of probe 41.

Figure 4:
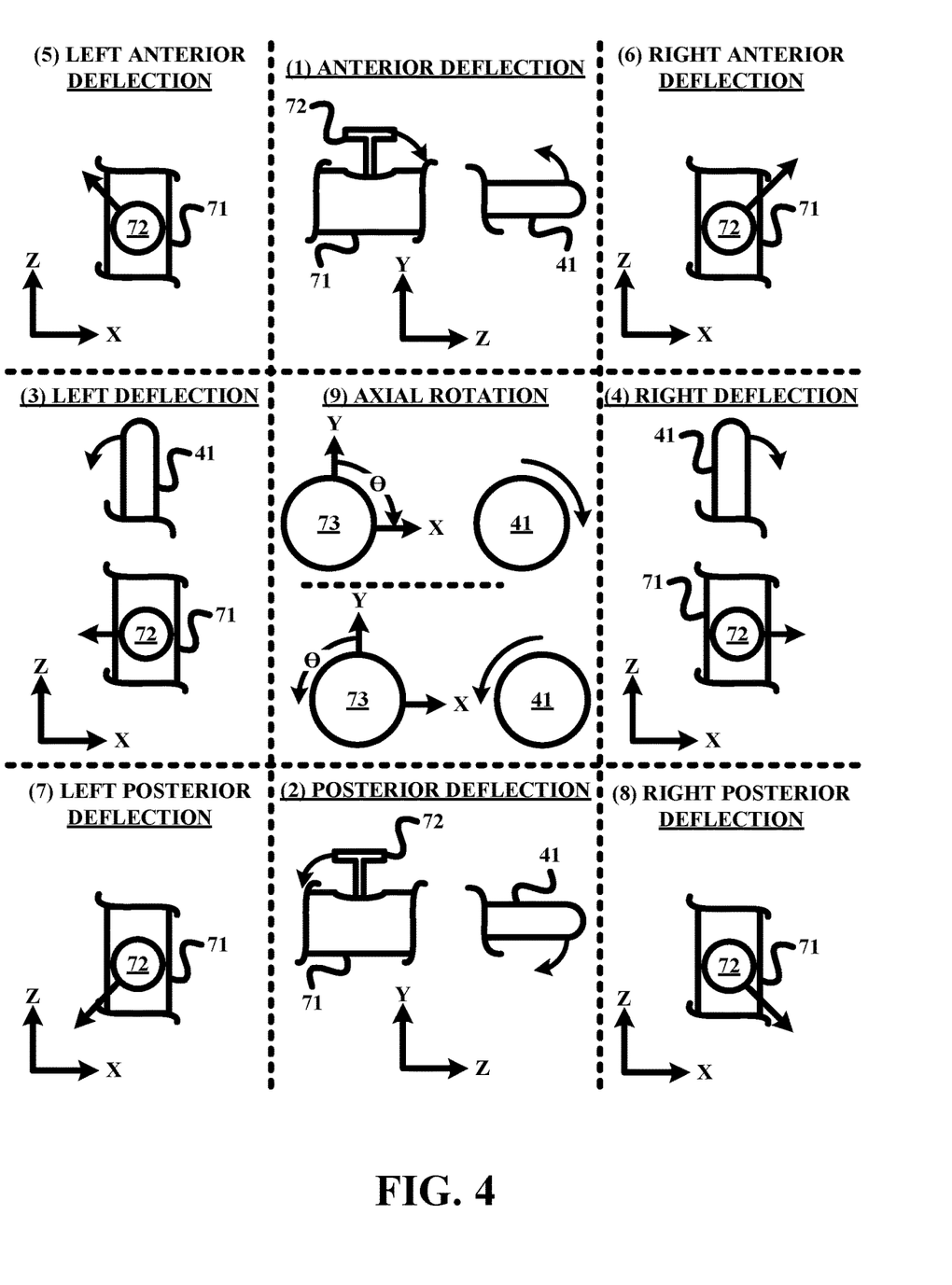
FIG. 4 illustrates an exemplary mapping of various movements of a probe of an TEE probe and a replica TEE control tool in accordance with the present invention.

For example, referring to FIG. 4 with control input device 72 in the form of a joystick:
  (1) an up +Z motion of the joystick is mapped to an anterior deflection of probe 41 as shown (or alternatively mapped to a posterior deflection of probe 41)
  (2) a down −Z motion of the joystick is mapped to the posterior deflection of probe 41 as shown (or alternatively mapped to the anterior deflection of probe 41);
  (3) a lateral left −X motion of the joystick is mapped to a lateral left deflection of probe 41 as shown;
  (4) a lateral left +X motion of the joystick is mapped to a lateral right deflection of probe 41 as shown;
  (5) a left upward motion of the joystick is mapped to a left anterior deflection of probe 41 as shown (or alternatively mapped to a left posterior deflection of probe 41);
  (6) a right upward motion of the joystick is mapped to a right anterior deflection of probe 41 as shown (or alternatively mapped to a right posterior deflection of probe 41);
  (7) a left downward motion of the joystick is mapped to a left posterior deflection of probe 41 as shown (or alternatively mapped to a left anterior deflection of probe 41); and
  (8) a right upward motion of the joystick is mapped to a right posterior deflection of probe 41 as shown (or alternatively mapped to a right anterior deflection of probe 41).

Referring back to FIG. 3, in practice, the mapping is stored within robotic workstation 62 whereby motion of the control input device 72 is communicated to robotic workstation 62 for the further communication of control commands to robotic actuator 50 for mapped movement of probe 41. Concurrently or alternatively, the mapping is stored within replica TEE control tool 70 whereby mapping data is communicated to robotic workstation 62 for the further communication of control commands to robotic actuator 50 for mapped movement of probe 41.

Still referring to FIG. 3, another inventive principle of the present invention is to install an electromechanical device 73 within replica control handle 71 to co-rotate with replica control handle 71 (i.e., a synchronized rotation of replica control handle 71 and electromechanical device 73 about a longitudinal axis of replica control handle 71 as symbolically shown by the dashed line extending through replica control handle 71). In practice, the co-rotation of electromechanical device 73 is communicated to robotic workstation 62 for the further communication of control commands to robotic actuator 50 for a corresponding rotation of probe 41 as exemplary shown in a (9) axial rotation of FIG. 4. Concurrently or alternatively, replica TEE control tool 70 generates rotation data indicative of a co-rotation of electromechanical device 73 whereby the rotation data is communicated to robotic workstation 62 for the further communication of control commands to robotic actuator 50 for corresponding rotation of probe 41 as exemplary shown in a (9) axial rotation of FIG. 4.

An unlimited example of electromechanical device is a three-axis accelerometer whereby a rotation of replica control handle 71 may be calculated using the data obtained from the three-axis accelerometer. This calculation may happen either on a microcontroller (not shown) within replica control handle 71 or within the robotic workstation 62.

The present invention provides multiple rotation modes, three (3) of which are now described herein.

Vertical Base Mode.

If replica control handle 71 is rotated to a certain delineated angle to vertical (e.g., 90° as shown in FIG. 4), then robot actuator 50 rotates probe 41 a corresponding rotational direction. If, for example, replica control handle 71 is rotated clockwise and reaches the desired threshold angle θ, then probe 41 is rotated clockwise, and if replica control handle 71 is rotated counter-clockwise and reaches the delineated threshold angle θ, then probe 41 is rotated counter-clockwise.

Fail Safe Mode.

To prevent an accidental rotation of replica control handle 71, a fail-safe (aka "dead man's switches") may be integrated into delineated degree mode of replica control handle 71. In this mode, robotic actuator 50 does not rotate probe 41 until replica control handle 71 is rotated past the delineated threshold angle and the fail safe is activated.

Relative Roll Mode.

A rotation activation of replica control handle 71 records a current roll position of replica control handle 71, but probe 41 is not actuated at that time. After rotation activation, when replica control handle 71 is then rotated past a delineated threshold angle from that recorded roll angle (e.g., 30°), then robotic actuator 50 rotates probe 41 in the corresponding direction (clockwise or counter-clockwise).

To facilitate a further understanding of the present invention, embodiments 50a and 70a of respective robot actuator 50 and replica control tool 70 will now be described herein.

Figure 5:
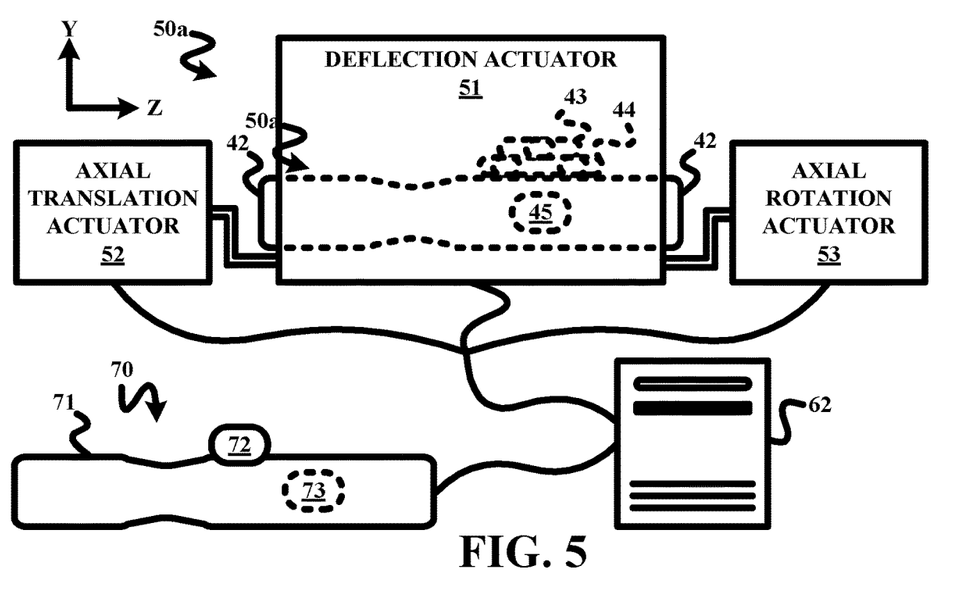
FIG. 5 illustrates an exemplary embodiment of a robotic actuator and a replica TEE control tool in accordance with the present invention.

Referring to FIG. 5, robotic actuator 50a employs a deflection actuator 51, an axial translation actuator 52, and an axial rotation actuator 53.

Deflection actuator 51 is mechanically engaged as known in the art with dials 43 and 44 of TEE probe 40. Workstation 62 provides control commands to motor controller(s) (not shown) of deflection actuator 51 for actuating dials 43 and 44 to execute a deflection of a probe 41 (not shown) of TEE probe 40 corresponding to a mapped motion of control input device 72 of replica control tool 70.

Axial translation actuator 52 and axial rotation actuator 53 are mechanically coupled to deflection actuator 51.

Axial translation actuator 52 as known in the art may be actuated to translate TEE control handle 42 along its longitudinal axis. Workstation 62 provides control commands to a motor controller (not shown) of axial translation actuator 52 to actuate an axial translation of TEE control handle 42.

Axial rotation actuator 53 as known in the art may be actuated to rotate TEE control handle 42 along its longitudinal axis. Workstation 62 provides control commands to a motor controller (not shown) of axial rotation actuator 53 to execute a rotation of TEE control handle 42 corresponding to a mapped rotation of electromechanical device 73 of replica control tool 70.

Figure 6:
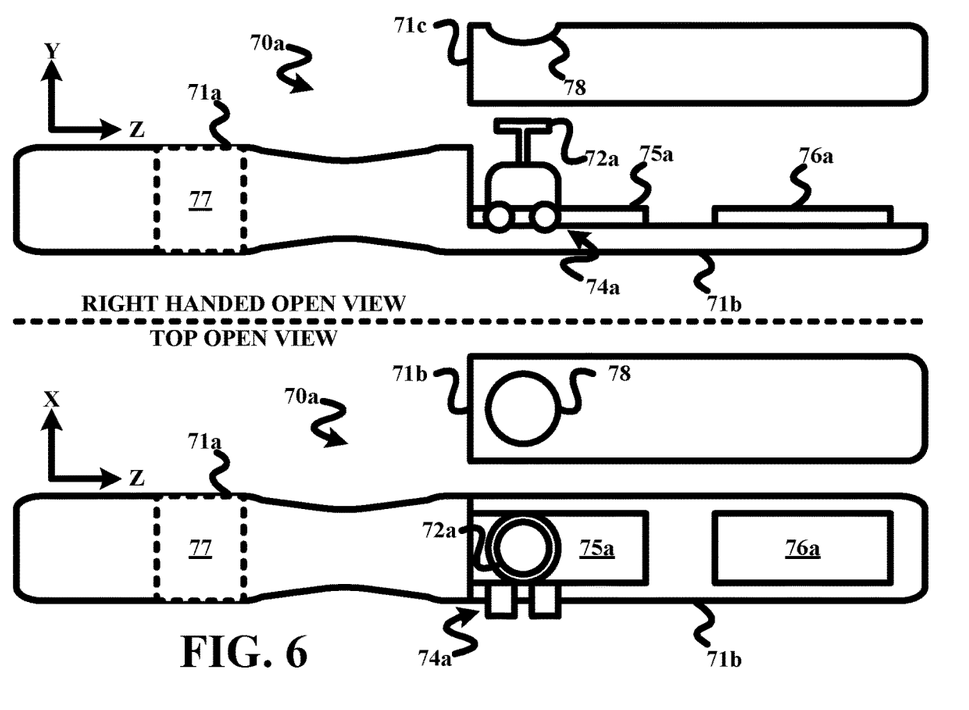
FIG. 6 illustrates an exemplary embodiment of the replica TEE control tool shown in FIG. 5 in accordance with the present invention.

Referring to FIG. 6, generally, a solid replica 70a of TEE control handle 42 is made by splitting an upper half 71a and a lower half 71b of TEE control handle 42 whereby electronic components 75a and 76a may be fitted and placed inside lower half 71b. Additionally, a hole 78 is made in a top cover 71c of lower half 71b to allow for a thumb joystick 72a to pass there through.

Lower half 71b contains cut-outs to house the electronics including a robotic actuator controller and a communication controller. Specifically, a printed circuit board ("PCB") 75a holds thumb joystick 72 (e.g., a two axis 30KΩ potentiometer) and a three-axis accelerometer (not shown) (e.g., a three-axis accelerometer from STMicroelectronics). PCB 75a also contains a robotic actuator controller in the form of a microcontroller chip (e.g., microcontroller manufactured by Renesas) to interpret signals from thumb joystick 72 and the accelerometer and to output data in appropriate format for workstation 62 (e.g., an I$^2$C format.) PCB 75a may be held securely in place by a PCB holder (not shown for clarity) that is inserted onto a keyed boss (not shown for clarity) on lower half 71b of replica control handle 70a. The PCB holder also holds two membrane switches 74a at a 90° angle from the joystick/accelerometer for use as buttons to replicate buttons 45 on TEE probe handle 42 (FIG. 5).

A second area of lower half 71b houses a communication controller 76a (e.g., a Teensy 3.0 microcontroller board). Communication controller 76a processes the I$^2$C input from the joystick, accelerometer, and buttons and output the data over a universal serial bus ("USB") to workstation 62 either as a simulated serial port or as a game controller, the latter allowing for easy integration into any software application. A channel and hole (not shown) is cut out an end of lower half 71b to allow wires to pass from controller 76a to workstation 62 and to house a USB connector.

Alternatively, the communication between replica control handle 70a and workstation 62 occurs through a wireless communication instead of wired USB. In the wireless mode, communication controller 76 is implemented as a wireless module (e.g., Bluetooth or Wi-Fi) and a battery pack. This embodiment allows for more freedom of motion and positioning.

Also alternatively, communication controller 76a may be omitted and PCB 75a may be equipped with communication components, and the controllers may be installed within workstation 62.

In practice, bosses (not shown) may be utilized to properly align cover 71c with lower half 71b, which may be secured to lower half 71b via screws.

Also, upper half 71a of replica control handle 70a may be solid and integrated with lower half 71b, or may be hollow and directly attached to lower half 71b via a threaded screw connector (not shown). The hollow embodiment of upper half 71a prevents replica control handle 70a from being top heavy.

Further, an LED or laser 77 may be placed within a hollow upper half 71a (e.g., with in a screw connector) whereby LED or laser 77 lights up to indicate to the user a specific event has occurred. For example, the LED/laser 77 may light up when a button 74a is pressed. A multi-color LED may be used to indicate different events. For example, one color may be used to indicate a button 74*a* has been pressed and another color may indicate the delineated threshold angle has been surpassed and TEE probe 40 is being rotated.

Still further, a vibration mechanism (not shown) may be the assembly to give the clinician/technician haptic feedback. This feedback can be used when specific events are triggered. For example, the replica can be made to vibrate when a button 74*a* is pressed, TEE probe 40 is being actuated, or when the force measure on TEE probe 40 exceeds a chosen threshold. For this embodiment, force feedback requires a force sensing technique implement by TEE probe 40, either through physical force sensors or by estimation of current forces using the measured currents drawn by the actuating motors.

Referring to FIGS. 1-6, those having ordinary skill in the art will appreciate numerous benefits of the present invention including, but not limited to, an intuitive remote control of a robotic actuator of an interventional tool of any type.

Furthermore, as one having ordinary skill in the art will appreciate in view of the teachings provided herein, features, elements, components, etc. described in the present disclosure/specification and/or depicted in the FIGS. 1-6 may be implemented in various combinations of electronic components/circuitry, hardware, executable software and executable firmware, particularly as application modules of a controller as described herein, and provide functions which may be combined in a single element or multiple elements. For example, the functions of the various features, elements, components, etc. shown/illustrated/depicted in the FIGS. 1-6 can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk read only memory (CD-ROM), compact disk read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of novel and inventive replica control tools, (which embodiments are intended to be illustrative and not limiting), it is noted that modifications and variations can be made by persons having ordinary skill in the art in light of the teachings provided herein, including the FIGS. 1-6. It is therefore to be understood that changes can be made into the preferred and exemplary embodiments of the present disclosure that are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. A replica control tool for remotely controlling a control handle of an interventional tool robotically controlled by a robotic actuator, the interventional tool including a flexible probe with a distal end, a control handle configured to be held by a user and including controls for manually controlling yaw and pitch of the flexible probe, the control handle being rotatable to rotate the flexible probe, the replica control tool comprising:

a replica control handle substantially being a replica of a structural configuration of the control handle of the interventional tool;

a control input device movable relative to the replica control handle to provide instructions to the robotic actuator to control the yaw and pitch of the flexible probe;

an electromechanical device co-rotatable with the replica control handle to sense rotation of the replica control handle and provide instructions to the robotic actuator to rotate the control handle of the interventional tool; and a robotic actuator controller operable in communication with the control input device of the replica control handle to remotely control a deflection of the distal end of the flexible probe responsive to movement of the control input device relative to the replica control handle and further operable in communication with the electromechanical device of the replica control handle to remotely control a rotation of a distal end of the interventional tool responsive to co-rotation of the electromechanical device and the replicable control handle.

2. The replica control tool of claim 1, wherein the robotic actuator controller is operable to remotely control an anterior deflection of a distal end of the interventional tool by the robotic actuator responsive to a movement of the control input device relative to the replica control handle mapped to at least one of:
   anterior deflection of the distal end of the interventional tool;
   posterior deflection of the distal end of the interventional tool;
   lateral deflection of the distal end of the interventional tool;
   lateral posterior deflection of the distal end of the interventional tool; and
   the lateral anterior deflection of the distal end of the interventional tool.

3. The replica control tool of claim 1, wherein the interventional tool handle includes dials for controlling the yaw and pitch of the flexible probe and the replica control handle input device includes a joystick or trackball to provide the instructions to the robotic actuator to control the yaw and pitch of the interventional tool flexible probe.

4. The replica control tool of claim 1, wherein the robotic actuator controller is operable to rotate the control handle of the interventional tool in one of at least three modes:
   a vertical base mode in which the replica control handle is rotated to a delineated angle to vertical and the robot actuator rotates the flexible probe in a corresponding rotational direction,
   a fail safe mode which prevents an accidental rotation of the replica control handle in the fail safe mode and in which the robotic actuator does not rotate the flexible probe until the replica control handle is rotated past a preselected threshold angle and the fail safe mode is active,
   a relative roll mode in which a rotation activation of the replica control handle records a current roll position of the replica control handle but the flexible probe is not actuated when the current roll position is recorded, after rotation activation when the replica control handle is then rotated past the threshold angle, the robotic actuator rotates the flexible probe in a corresponding clockwise or counter-clockwise direction.

5. A replica control tool, for remotely controlling a control handle of an interventional tool robotically controlled by a robotic actuator, the interventional tool including a flexible probe with a distal end, a control handle configured to be held by a user and including controls for manually controlling yaw and pitch of the flexible probe, the control handle being rotatable to rotate the flexible probe, the replica control tool comprising:
   a replica control handle substantially being a replica of a structural configuration of the control handle of the interventional tool;
   a control input device movable relative to the replica control handle to provide instructions to the robotic actuator to control the yaw and pitch of the flexible probe, wherein the control input device is one of a joystick, a tracker ball and at least one dial;
   an electromechanical device co-rotatable with the replica control handle to sense rotation of the replica control handle and provide instructions to the robotic actuator to rotate the control handle of the interventional tool, wherein the electromechanical device is a three axis accelerometer; and
   a robotic actuator controller operable in communication with the control input device of the replica control handle to remotely control a deflection of the distal end of the flexible probe responsive to movement of the control input device relative to the replica control handle and further operable in communication with the electromechanical device of the replica control handle to remotely control a rotation of a distal end of the interventional tool responsive to co-rotation of the electromechanical device and the replicable control handle.

6. The replica control tool of claim 1, wherein the robotic actuator controller remotely controls the rotation of the distal end of the interventional tool by the robotic actuator responsive to the co-rotation of the electromechanical device with the replica control handle when the rotation of the replica handle equals or exceeds a preselected degree of rotation.

7. The replica control tool of claim 1, wherein the robotic actuator controller is enabled to control the rotation of the flexible probe clockwise or counter-clockwise by rotating the replica control handle to a preselected vertical angle.

8. The replica control tool of claim 1, wherein the interventional tool is one of a catheter and a flexible scope.

9. A robotic actuation system, comprising:
   a robotic actuator operable to robotically control a control handle of an interventional tool, the interventional tool including a flexible probe with a distal end, a control handle configured to be held by a user and including controls for manually controlling yaw and pitch of the flexible probe, the control handle being rotatable to rotate the flexible probe; and
   a replica control tool including
      a replica control handle substantially being a replica of a structural configuration of the control handle of the interventional tool;
      a control input device movable relative to the replica control handle to provide instructions to the robotic actuator to control the yaw and pitch of the flexible probe;
      an electromechanical device co-rotatable with the replica control handle to sense rotation of the replica control handle and provide instructions to the robotic actuator to rotate the control handle of the interventional tool;
   a robotic actuator controller, the robotic actuator controller being operable in communication with the control input device and the robotic actuator to remotely control a deflection of the distal end of the flexible probe of the interventional device by the robotic actuator responsive to any movement of the control input device relative to the replica control handle, and being further operable in communication with the electromechanical device and the robotic actuator to remotely control a rotation of a distal end of the interventional tool by the robotic actuator responsive to a co-rotation of the electromechanical device with the replicable control handle.

10. The robotic actuation system of claim 9, wherein the robotic actuator controller is operable to remotely control a deflection of a distal end of the interventional tool by the robotic actuator responsive to a movement of the control input device relative to the replica control handle mapped to:
  an anterior deflection of the distal end of the interventional tool;
  a posterior deflection of the distal end of the interventional tool;
  a lateral deflection of the distal end of the interventional tool;
  a lateral anterior deflection of the distal end of the interventional tool; and
  a lateral posterior deflection of the distal end of the interventional tool.

11. The robotic actuation system of claim 9, wherein the control input device is one of a joystick, a tracker ball and at least one dial; and
  wherein the electromechanical device is a three-axis accelerometer.

12. The robotic actuation system of claim 9, wherein the interventional tool handle includes dials for controlling the yaw and pitch of the flexible probe and the replica control handle input device includes a joystick or trackball to provide the instructions to the robotic actuator to control the yaw and pitch of the interventional tool flexible probe.

13. The robotic actuation system of claim 9, wherein the robotic actuator controller is operable to remotely rotate the control handle of the interventional tool in one of at least three modes:
  a vertical base mode in which the replica control handle is rotated to a delineated angle to vertical and the robot actuator rotates the flexible probe in a corresponding rotational direction,
  a fail safe mode which prevents an accidental rotation of the replica control handle in the fail safe mode and in which the robotic actuator does not rotate the flexible probe until the replica control handle is rotated past a preselected threshold angle and the fail safe mode is active,
  a relative roll mode in which a rotation activation of the replica control handle records a current roll position of the replica control handle but the flexible probe is not actuated at that time, after rotation activation when the replica control handle is then rotated past the threshold angle, the robotic actuator rotates the flexible probe in a corresponding clockwise or counter-clockwise direction.

14. The robotic actuation system of claim 9, wherein the robotic actuator controller remotely controls the rotation of the distal end of the interventional tool by the robotic actuator responsive to the co-rotation of the electromechanical device with the replica control handle when the rotation of the replica handle equals or exceeds a preselected degree of rotation.

15. The robotic actuation system of claim 9, wherein the replica control tool further includes:
  wherein the robotic actuator controller is enabled to control the rotation of the flexible probe clockwise or counter-clockwise by rotating the replica control handle to a preselected vertical angle before rotating the replica control handle.

16. The robotic actuation system of claim 9, wherein the interventional tool is one of a catheter and a flexible scope.

* * * * *